(12) United States Patent
Fritsch (10) Patent No.: US 9,015,886 B2
(45) Date of Patent: Apr. 28, 2015

(54) ORAL CARE IMPLEMENT

(71) Applicant: Braun GmbH, Kronberg (DE)

(72) Inventor: Thomas Fritsch, Eppstein (DE)

(73) Assignee: Braun GmbH, Kronberg (DE)

( * ) Notice: Subject to any disclaimer, the term of this patent is extended or adjusted under 35 U.S.C. 154(b) by 17 days.

(21) Appl. No.: 13/920,184

(22) Filed: Jun. 18, 2013

(65) Prior Publication Data

US 2013/0340184 A1 Dec. 26, 2013

(30) Foreign Application Priority Data

Jun. 20, 2012 (EP) ..................................... 12172726
May 21, 2013 (EP) ..................................... 13168496

(51) Int. Cl.
*A61C 17/34* (2006.01)
*A46B 15/00* (2006.01)
*A61C 17/22* (2006.01)
*A46B 5/00* (2006.01)

(52) U.S. Cl.
CPC ............... *A61C 17/34* (2013.01); *A46B 5/0062* (2013.01); *A46B 15/0012* (2013.01); *A61C 17/221* (2013.01); *A61C 17/3418* (2013.01)

(58) Field of Classification Search
USPC ............... 15/167.1, 172, 143.1, 144.1, 176.1, 15/201, 22.1, 22.2, 21.1
See application file for complete search history.

(56) References Cited

U.S. PATENT DOCUMENTS

| 5,315,732 A | * | 5/1994 | Huefner et al. ............... 15/167.1 |
| 5,765,254 A | * | 6/1998 | O'Halloran .................. 15/167.1 |
| 8,631,532 B2 | * | 1/2014 | Utsch et al. .................... 15/22.1 |

* cited by examiner

*Primary Examiner* — Shay Karls
(74) *Attorney, Agent, or Firm* — Vladimir Vitenberg (57) ABSTRACT

An oral care implement is disclosed. The oral care implement includes a head section including a carrier element that is mounted for driven movement; a base section including a transmission element; and an at least partly elastically deformable neck section arranged between the head section and the base section. The transmission element is coupled to the carrier element for driving the carrier element into an oscillatory movement with an oscillation amplitude peak value. Further, the neck section is arranged as a parallel spring arrangement that deforms when a load above a first threshold load value is applied at the head section along a use direction such that the angular relationship between the head section and the base section is preserved and the head section and the base section move relatively to each other resulting in a reduction of the oscillation amplitude peak value.

14 Claims, 6 Drawing Sheets

ORAL CARE IMPLEMENT

FIELD OF THE INVENTION

The present disclosure relates to oral care implements that have a head section, a neck section, and a base section, where the neck section connects the head section and the base section. More particularly, the present disclosure relates to oral care implements having a neck section at least partly elastically deformable under a load applied at the head section along a use direction.

BACKGROUND OF THE INVENTION

Oral care implements such as replacement brush heads for an electric toothbrush are known that have a head section, a neck section, and a base section (for example, a handle section or housing section), where the neck section is arranged to be at least partly elastically deformable under a load applied at the head section along a use direction. It is known that the deformation of the neck section leads to a bending of the head section relative to the base section. Thus, the intended angle under which the head section should be applied for treatment of the oral cavity changes under an applied load and further the user does not necessarily note this bending as the head section may be located inside of the oral cavity when the load is applied.

Accordingly, there is a need for an oral care implement that is improved over the known oral care implements.

SUMMARY OF THE INVENTION

In one embodiment, an oral care implement is provided. The oral care implement includes a head section including a carrier element that is mounted for driven movement; a base section including a transmission element; and an at least partly elastically deformable neck section arranged between the head section and the base section. The transmission element is coupled to the carrier element for driving the carrier element into an oscillatory movement with an oscillation amplitude peak value. Further, the neck section is arranged as a parallel spring arrangement that deforms when a load above a first threshold load value is applied at the head section along a use direction such that the angular relationship between the head section and the base section is preserved and the head section and the base section move relatively to each other resulting in a reduction of the oscillation amplitude peak value.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

Example embodiments of oral care implements in accordance with the present disclosure are discussed below. An oral care implement may be realized as an oral care device or as an oral care attachment. With "oral care device" a device is meant that can be operated without further addition, while an "oral care attachment" is intended to be attached to a handle section such that the oral care attachment and the handle section form an oral care device in the attached state. For sake of clarity, an oral care device does not need to have an oral care attachment.

According to the present disclosure, an oral care implement having a head section, a base section, and a neck section that connects the head section and the base section, respectively is provided. In one embodiment, the neck section may be arranged to be deformable under a load that is applied at the head section along a use direction (for example, by pressing the head section against a surface in the oral cavity such as a tooth surface for cleaning purposes). The use direction is essentially perpendicular to a longitudinal extension axis of the oral care implement. Without limitation, an oral care implement may be a manual toothbrush, an electric toothbrush, a manual or electric flossing device, a manual or electric tongue cleaning device, a replaceable oral treatment attachment such as a replaceable brush head, tongue cleaning head, or flossing head. In one embodiment, the neck section of the proposed oral care implement is arranged to be at least partly elastically deformable such that the head section moves relative to the handle section or housing section, respectively, under a load applied along the use direction essentially without changing the angular relationship between the head section and the base section. The deforming portion of the neck section is arranged as a parallel spring arrangement. With such a parallel spring arrangement, the angle under which the head section is applied for treating the oral cavity is not changed under an applied load (i.e. the angular relationship between the head section and the housing section is preserved).

The parallel spring arrangement may comprise one, two or more spring elements. In case of two or more spring elements, the spring elements are arranged parallel to each other. The spring element or spring elements may in particular be parallel to a longitudinal extension axis or a transmission element axis of the oral care implement. The spring element or spring elements may further be arranged transverse to the use direction. In some embodiments, the spring element or spring elements may be at least partly realized as flat plastic or metal sheet members or as a combination of flat plastic and metal sheet members. In some embodiments, the neck section may comprise at least a soft material membrane, which soft material membrane may connect two spring elements and the soft material membrane may be arranged to shield a hollow interior of the oral care implement.

In some embodiments, the neck section may include a biasing element such as a biasing spring that applies a biasing load in a direction opposite to the use direction. In some embodiments, the neck section may comprise a stop element that essentially inhibits a deformation of the neck section under the applied biasing load. The biasing load may be chosen such that the load applied at the head section along the use direction leads only to a deformation of the neck section when the applied load is above a non-zero first threshold load value.

In one embodiment, the head section includes a carrier element mounted for driven oscillatory motion with an oscillation peak amplitude value, which carrier element is coupled or may be arranged for being coupled with a transmission element. A transmission element may be a drive shaft or a drive shaft extension element. A "drive shaft" shall be considered to be coupled to a drive unit for transmitting a motion from the drive unit to the carrier element. A "drive shaft extension element" shall be considered to be connectable to a drive shaft or a drive unit for transmitting motion from the drive unit to the carrier element. The neck section is arranged to be deformable under a load applied at the head section along a use direction as described before. The transmission element may be mounted at the base section for movement with a fixed relationship to the base section, which fixed relationship remains unaffected from any deformation of the neck section. When the neck section deforms, the carrier element and the transmission element move relative to each other and they are arranged such that the oscillation amplitude peak value of the oscillatory motion is reduced when the load applied at the head section along a use direction is above a first threshold load value.

In one embodiment, the carrier element and the transmission element may be arranged such that the transmission element decouples from the carrier element when the load applied at the head section is above a second threshold load value. The parallel spring arrangement may have one or all of the features discussed above. The first threshold load value may be zero Newtons (N) or may be above 0 N, for example, the first threshold load value may be chosen to lie in a range between about 0.5 N and about 2.5 N or between about 1.0 N and about 2.0 N. A biasing load as described before can be utilized to define the non-zero first threshold load value. In some embodiments, the second threshold load value may be chosen to lie in a range of between about 2.5 N and about 6.0 N, or, in another embodiment, between about 3.0 N and about 5.0 N.

In some embodiments, an adjustment element may be provided by which a user can apply a force upon the head section along the use direction such that the neck section deforms. As discussed above, the oral care implement is arranged such that the oscillation peak amplitude value is reduced when the applied force is above a first threshold value. By such an adjustment element, the user can set a preferred oscillation peak amplitude value. In some embodiments, the adjustment element may be manually operable; in particular the adjustment element may be realized as a slider element by which a wedge movably mounted at the base section can be slid towards the head section to thereby apply an increasing force onto the head section along the use direction.

In some embodiments, the carrier element is driven into an oscillatory movement having an oscillation angle that may be 50 degrees (i.e. ±25 degrees around a center position). In a state at which a medium load (for example, half of the value that may be considered a high load value) is applied onto the head section along the use direction, the oscillation angle may be reduced to about 32 degrees (i.e. about ±16 degrees around a center position). In a state in which a high load is applied at the head section along the use direction, the oscillation angle may be reduced to about 23.9 degrees (i.e. about ±11.95 degrees around a center position). In other words, the oscillation angle (and thus also the oscillation amplitude peak value) may be reduced to about 50% or less under application of a high load applied at the head section along the use direction. The high load mentioned here may in particular be identical to the second threshold load value. It is noted that while in the following reference is made to a housing section when an oral care attachment is discussed and to a handle section when an oral care device is discussed, both sections have in common that they are relatively fixed with respect to a users hand holding an oral care implement and thus each one of the sections alone or when attached together realize the "base section" mentioned in the previous paragraphs.

It is further noted that all of the features described in the present description, whether alone or in combination with other features, are considered to be freely combinable with each other in all ways obvious to a skilled person as long as such combination does not contradict the gist and scope of the present disclosure.

Figure 1:
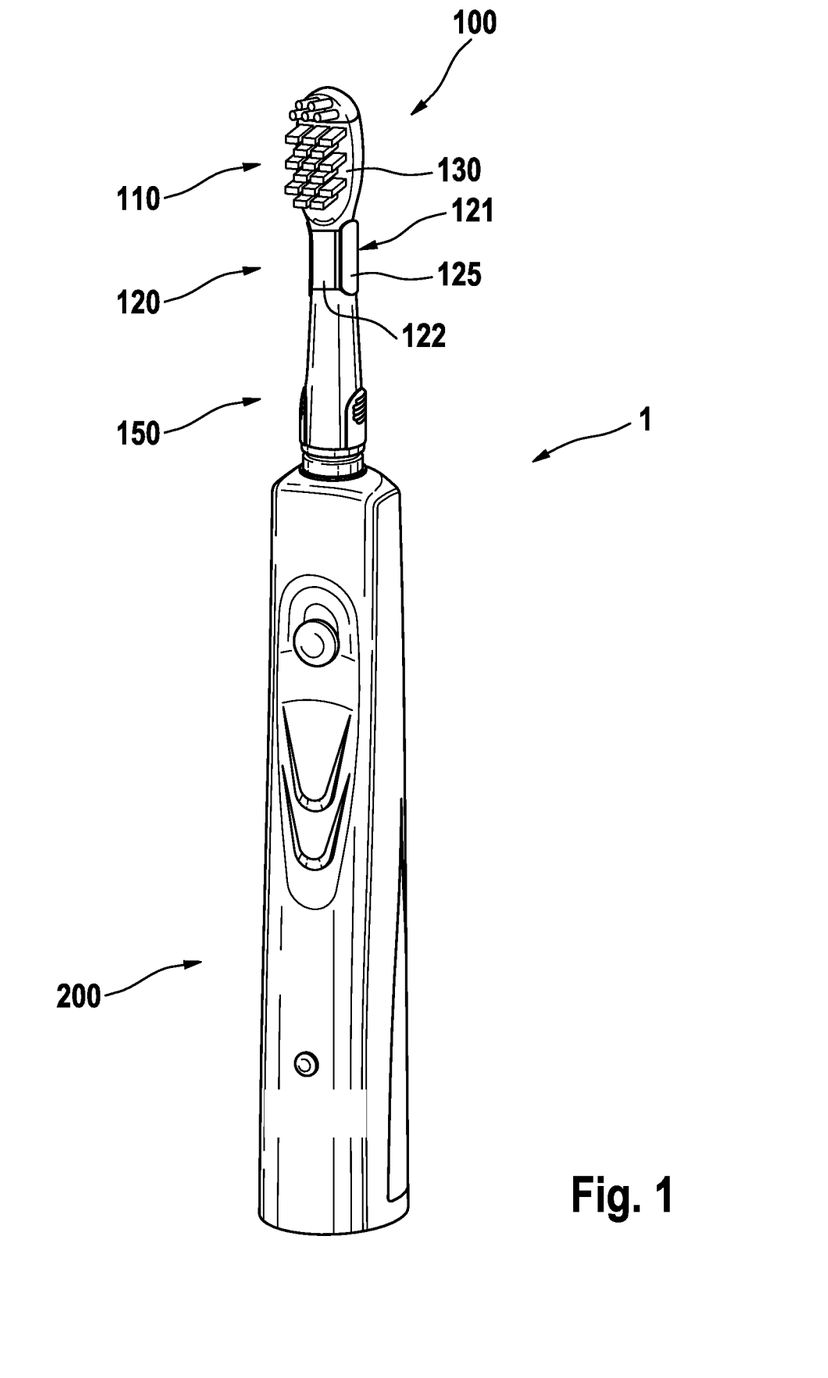
FIG. 1 is a depiction of an oral care implement according to embodiments shown and described herein.

FIG. 1 is a depiction of an example embodiment of an oral care implement 1 in accordance with the present disclosure. The oral care implement 1 is realized as an oral care device, in particular an electric toothbrush. In other embodiments, the oral care device may be realized as a manual toothbrush, a manual or electric flosser or a manual or electric tongue cleaner. In one embodiment, the oral care device 1 may have a base section 200 (here realized as the handle section of the oral care device), a head section 110, and a neck section 120. In some embodiments, the head section 110 and the neck section 120 may be part of an oral care implement such as a replaceable oral care attachment 100. The head section 110 may include a carrier element 130 that may be mounted at the head section 110 for driven movement. The handle section 200 may include a drive unit for driving a transmission element (for example, a drive shaft) into an oscillatory movement, for example, an oscillatory rotation around the longitudinal transmission element axis or an oscillatory displacement along the longitudinal transmission element axis. The transmission element may be coupled with the carrier element 130 such that the carrier element 130 is driven into an oscillatory movement around and/or along a carrier axis 139. In some embodiments, the carrier axis may be parallel to the longitudinal transmission element axis, while in other embodiments the carrier axis may be transverse to the longitudinal transmission element axis. This will be explained in more detail for example embodiments with respect to FIGS. 2A and 2B in the following.

As mentioned, the oral care device 1 may include a detachable oral care attachment 100, which may include the head section 110 and the neck section 120. The oral care attachment 100 may further include a base section realized as a housing section 150 that is intended for being detachably secured to a handle section of the oral care device 1 in the attached state such that no relative movement is allowed between the housing of the handle section and the housing section of the oral care attachment 100. In such an embodiment, the housing section 150 of the oral care attachment 100 is a base section in the detached state and the housing section 150 and the handle section 200 together realize the base section of the oral care device 1 in the attached state. The head section 110 and the housing section 150 may be connected by the neck section 120. Then the housing section 150 may be considered as a part of the handle section 200.

The neck section 120 may be arranged so as to be deformable under a load applied at the head section 110 (as will be explained in more detail with respect to FIGS. 2A and 2B). In some embodiments, the neck section may be equipped with a parallel spring arrangement that may have two parallel arranged flat spring elements 121 and 122 that may be connected by a flexible soft material membrane 125 that reversibly deforms when the springs elastically deform under a load applied at the head section 110 along a use direction.

Figure 2A:
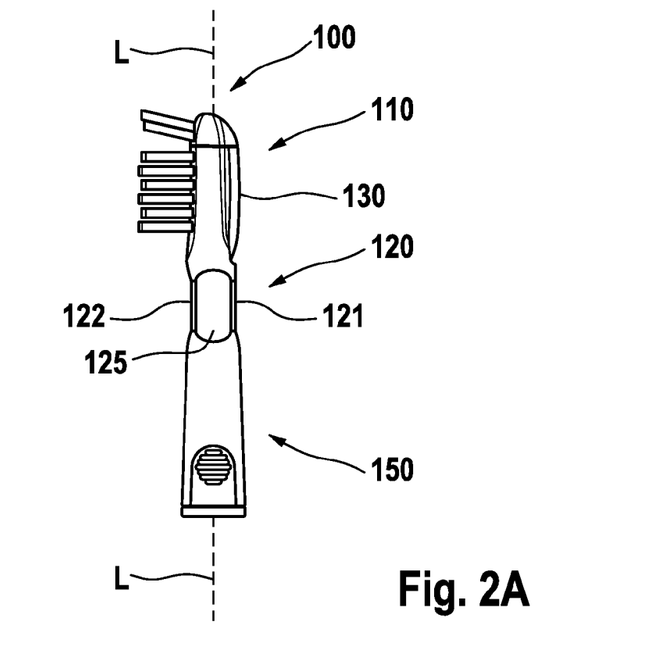
FIG. 2A is a side view of an oral care implement in an unloaded state according to embodiments shown and described herein.

FIG. 2A is a side view onto an example embodiment of an oral care implement realized as an oral care attachment 100 in accordance with the present disclosure. FIG. 2A shows the oral care attachment 100 in an unloaded state, i.e. in a state where no load is applied at the head section 110. The oral care attachment 100 generally extends along a longitudinal extension axis L indicated by a dashed line. The head section 110 may include a carrier element 130 that may be mounted for driven movement. In an attached state, when the oral care attachment 100 is attached to a handle section 200 of an oral care device, similarly as is shown in FIG. 1, a drive shaft of a drive unit may be coupled to the carrier element 130 for driving the carrier element into an oscillatory movement with an oscillation amplitude peak value, for example, into an oscillatory rotation around a carrier axis that may be parallel to the longitudinal extension axis L. The longitudinal extension axis L may in an attached state of the oral care attachment 100 coincide with a longitudinal transmission element axis of the transmission element.

As was discussed with reference to FIG. 1, the oral care attachment 100 includes a neck section 120 that connects the head section 110 and a housing section 150, which forms a base section of the oral care attachment. The neck section 120 may be arranged so as to be deformable under a load applied at the head section 110 along a use direction F (as indicated in FIG. 2B). In some embodiments, the neck section 120 may include two parallel arranged spring elements 121 and 122, which spring elements 121 and 122 may be flat. The housing section 150 and the head section 110 may be made from a hard plastic material such as POM (polyoxymethylene), PA (polyamide) ASA (acrylonitrile styrene acrylate), ABS (acrylonitrile-butadiene styrene) or PP (polypropylene). In some embodiments, the spring elements 121 and 122 may be made from the same hard plastic material (in particular in case of POM or PA) and may be realized as integral parts together with the respective hard plastic parts of the housing section 150 and the head section 110, for example, made in a plastic injection molding process.

In some embodiments, the spring elements 121 and 122 may be flat leaf springs made from a metal such as sheet steel. In some embodiments, the spring elements 121 and 122 may be connected by a flexible membrane 125 so that the hollow interior of the oral care attachment 100 is shielded. The flexible membrane may, for example, be made from a TPE (thermoplastic elastomer), a NBR (nitrile butadiene rubber), a LSR (liquid silicone rubber) or a similar flexible material. The flexible membrane may be connected to a hard plastic part, for example, the head section 110 and the neck section 120) by means of a form fit (in particular in case POM is used as hard plastic) or it may be connected by means of adhesion. The flexible membrane (whether connected by form-fit or adhesion) may be provided in an injection molding step or in an assembly step (i.e. as an independently manufactured part).

Figure 2B:
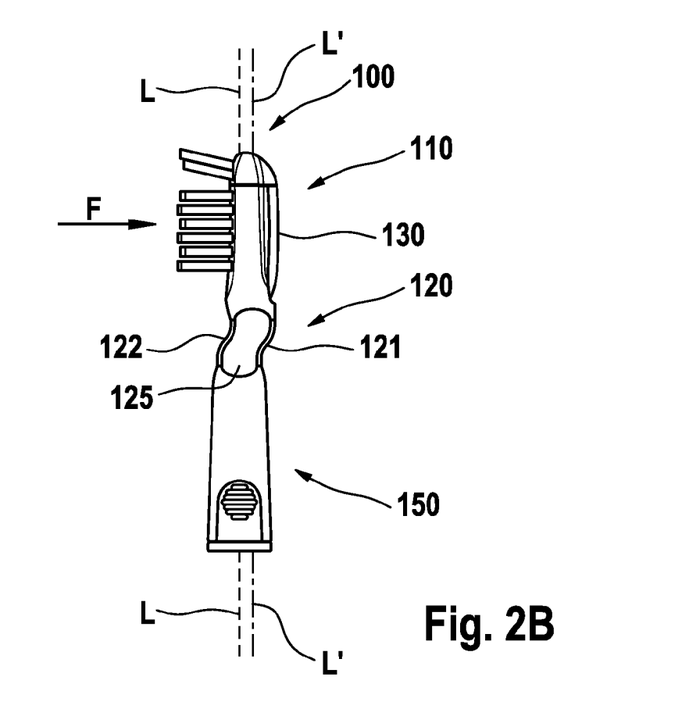
FIG. 2B is a side view of the oral care implement shown in FIG. 2A in a loaded state where the load applied at a head section is above a first threshold load value and has thus resulted in a deformation of a neck section.

FIG. 2B is a side view onto the oral care attachment 100 shown in FIG. 2A but in a state where a load is applied at the head section 110 along a use direction F that is essentially perpendicular to the longitudinal extension axis L. Under the applied load, the parallel spring elements 121 and 122 have deformed. The two parallel spring elements 121 and 122 form a "parallel guide structure" so that the relative movement of head section 110 and housing section 150 occurs without or at least with only a limited angular offset between these two sections. Considering the axis of the longitudinal extension axis L shown in FIG. 2A as being fixed in the head section 110, this axis is then parallel shifted into axis L' indicated by a dashed-dotted line in FIG. 2B. Due to the elastic properties of the spring elements 121 and 122, the deformation of the neck section 120 reversibly reduces to the unloaded state shown in FIG. 2A (i.e. the rest state of the spring elements 121 and 122) when the applied load is taken away. The flexible membrane 125 is arranged to follow the deformation of the spring elements 121 and 122.

Figure 3A:
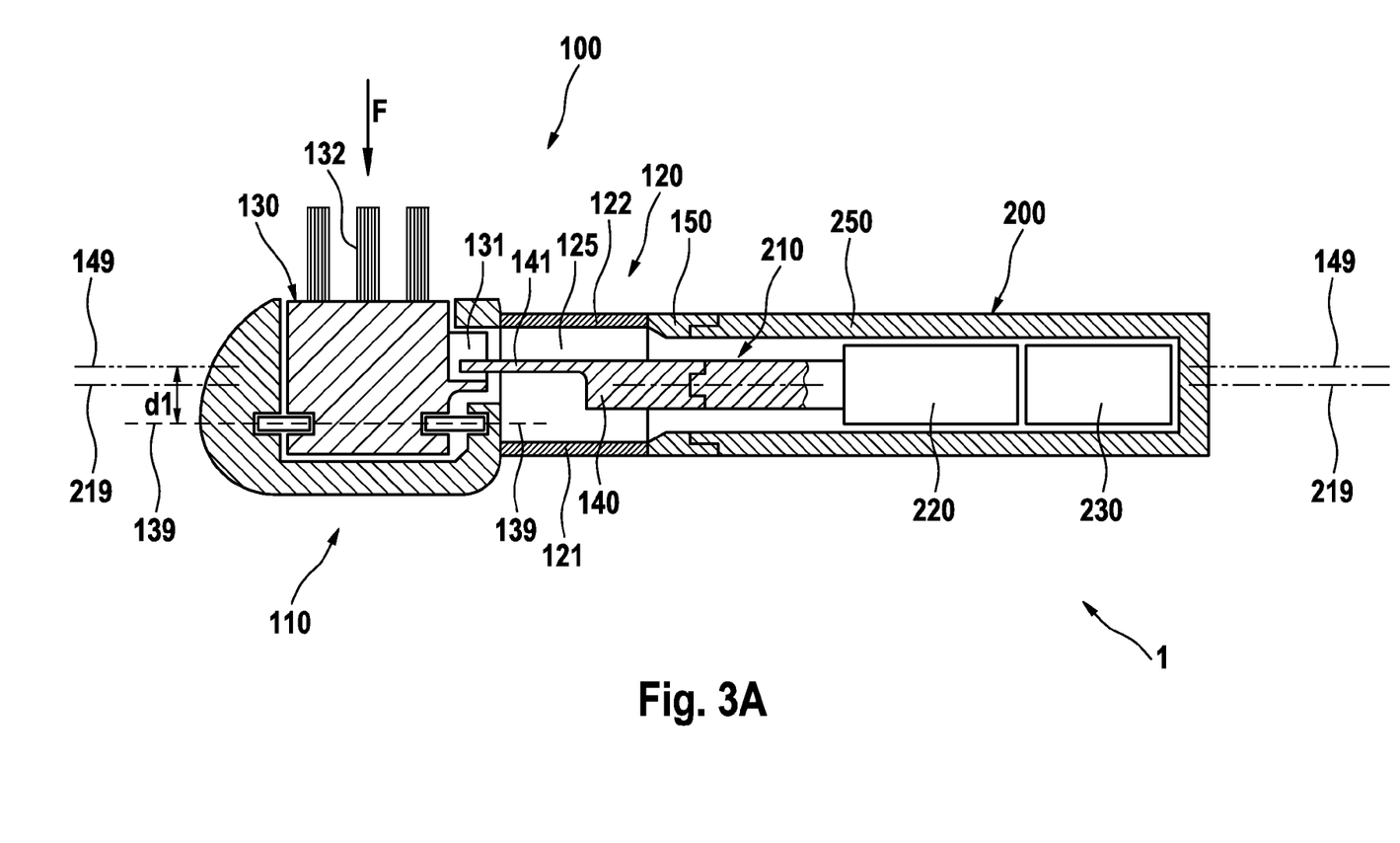
FIG. 3A is a longitudinal cross sectional cut through an example embodiment of an oral care implement in an unloaded state according to embodiments shown and described herein.

FIG. 3A is a schematic longitudinal cross section cut through an example embodiment of an oral care device 1 in accordance with the present disclosure. The oral care device may include a handle section 200 and a replaceable oral care attachment 100, while in other embodiments the oral care device may be an integral device without a replaceable oral care attachment. The oral care device 1 includes a head section 110 and a neck section 120. A carrier element 130 may be mounted at the head section 120 so that it can be driven into an oscillatory motion around a carrier axis 139. The handle section 200 may include a drive unit 220 for driving a transmission element 210 (for example, a drive shaft) into an oscillatory motion around a longitudinal transmission element axis 219. In other embodiments, the oscillatory motion of the transmission element may be along the longitudinal transmission element axis. The transmission element 210 may be coupled to the carrier element 130. In some embodiments as shown, the transmission element 210 may have a cam 141 that eccentrically projects away from the transmission element 210 along a cam axis 149 that is parallel to the longitudinal transmission element axis 219. In operation, when the transmission element 210 is driven into an oscillatory motion around the longitudinal transmission element axis 219, the cam 141 moves around the longitudinal transmission element axis 219 along an arc. The cam 141 may engage into a slot 131 provided in the carrier element 130. The cam 141 may snugly fit into the slot 131 in a circumferential direction but may be arranged to be movable in radial direction. When the cam 141 moves along the arc around the longitudinal transmission element axis 219, the moving cam 141 also moves the carrier element 130 around the carrier axis 139 due to the snug fit of cam 141 and slot 131 in circumferential direction. The distance between the carrier axis 139 and the cam axis 149 in the unloaded state, i.e. in a state where no load is applied onto the head section 110 along a use direction F, is d1.

In one embodiment, the neck section 120 may be arranged so as to be deformable when a load is applied onto the head section 110 along the use direction F. The neck section 120 therefore includes a parallel spring arrangement that in one example has two parallel spring elements 131 and 132. This enables that the deformation of the neck section 120 under an applied load preserves the angle between the drive shaft axis 219 and the carrier axis 139. In other embodiments, an alternative "parallel guide structure" comprises parallel arranged guide arms that are pivotably mounted on each end on the head section and on the base section such that under a load applied at the head section along the use direction, the head section and the base section move relatively to each other under preservation of their angular relationship. This parallel guide structure may in addition comprise one or more spring elements that elastically restore the unloaded relative positions of the head section and of the base section when the applied load is taken away.

Figure 3B:
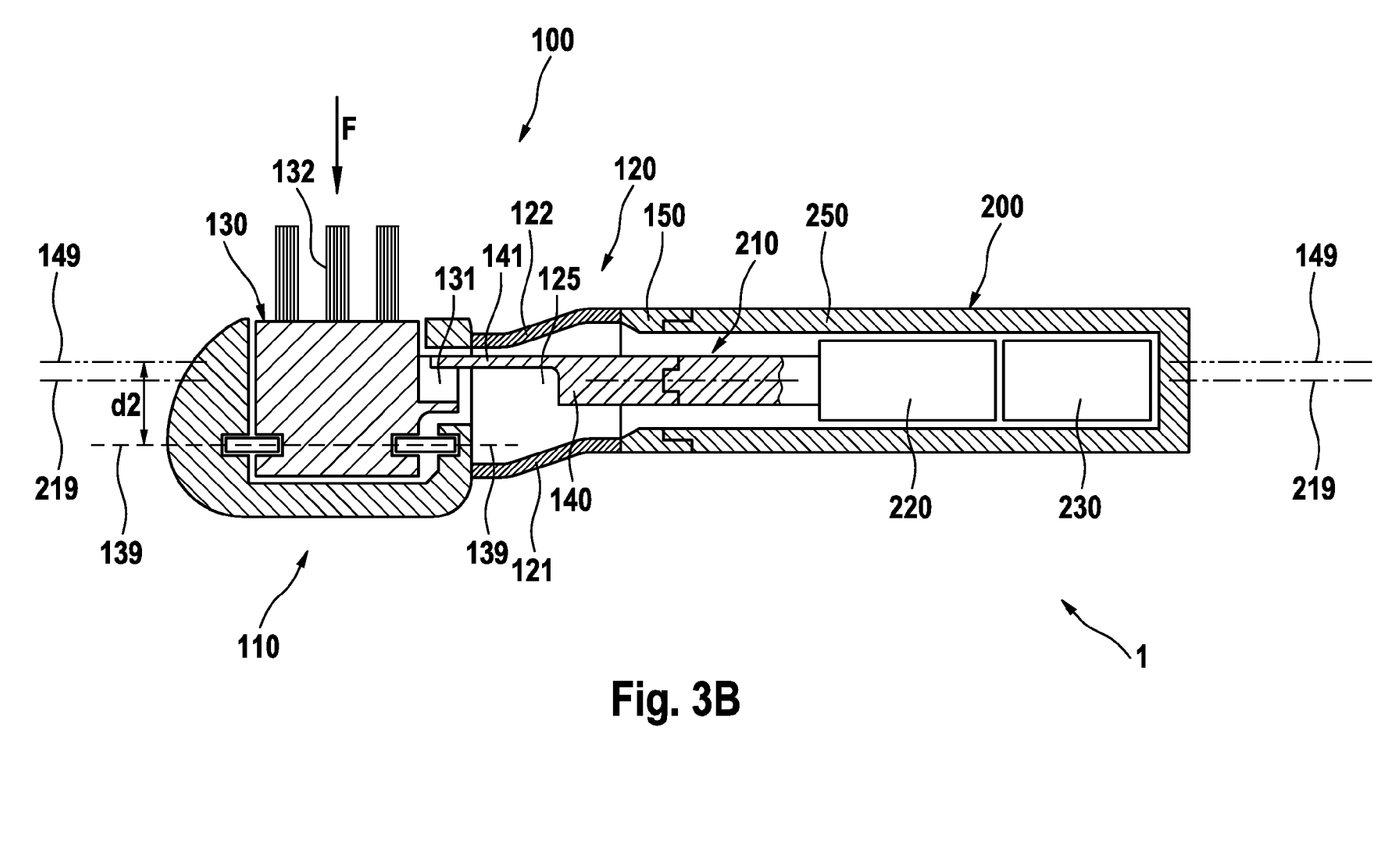
FIG. 3B is a longitudinal cross sectional cut through the oral care device shown in FIG. 3A in a loaded state where the load applied at the head section along a use direction is larger than a first threshold load value and has thus resulted in a deformation of the neck section.

FIG. 3B shows the same cross section as in FIG. 3A but in a loaded state when a load is applied onto the head section 110 along the use direction F. The parallel spring elements 121 and 122 are bent. The cam 141 still engages with the slot 131 and moves the carrier element 130 into an oscillatory motion around the carrier axis 139. But due to the deformation of the neck section 120 under the applied load the distance between the cam axis 149 and the carrier axis 139 has increased to d2, where d2>d1. Thus, the oscillation amplitude peak value of the oscillatory movement of the carrier element 130 has decreased in contrast to the unloaded state shown in FIG. 3A. Hence, the oral care device as described automatically reduces the oscillation amplitude peak value of the oscillatory movement of the carrier element 130 around the carrier axis 139 under application of a load along the use direction F onto the head section 110. The higher the applied load the larger the deformation and the larger the reduction of the oscillation amplitude peak value of the oscillatory movement of the carrier element 130 around the carrier axis 139. The cam 141 and the slot 131 may be sized such that the cam 141 disengages from the slot 131 at a given second threshold load value. The second threshold load value may be chosen to lie in a range of between about 2.5 Newton and about 6.0 Newton, in another embodiment, between about 3.0 Newton and about 5.0 Newton.

Figure 4:
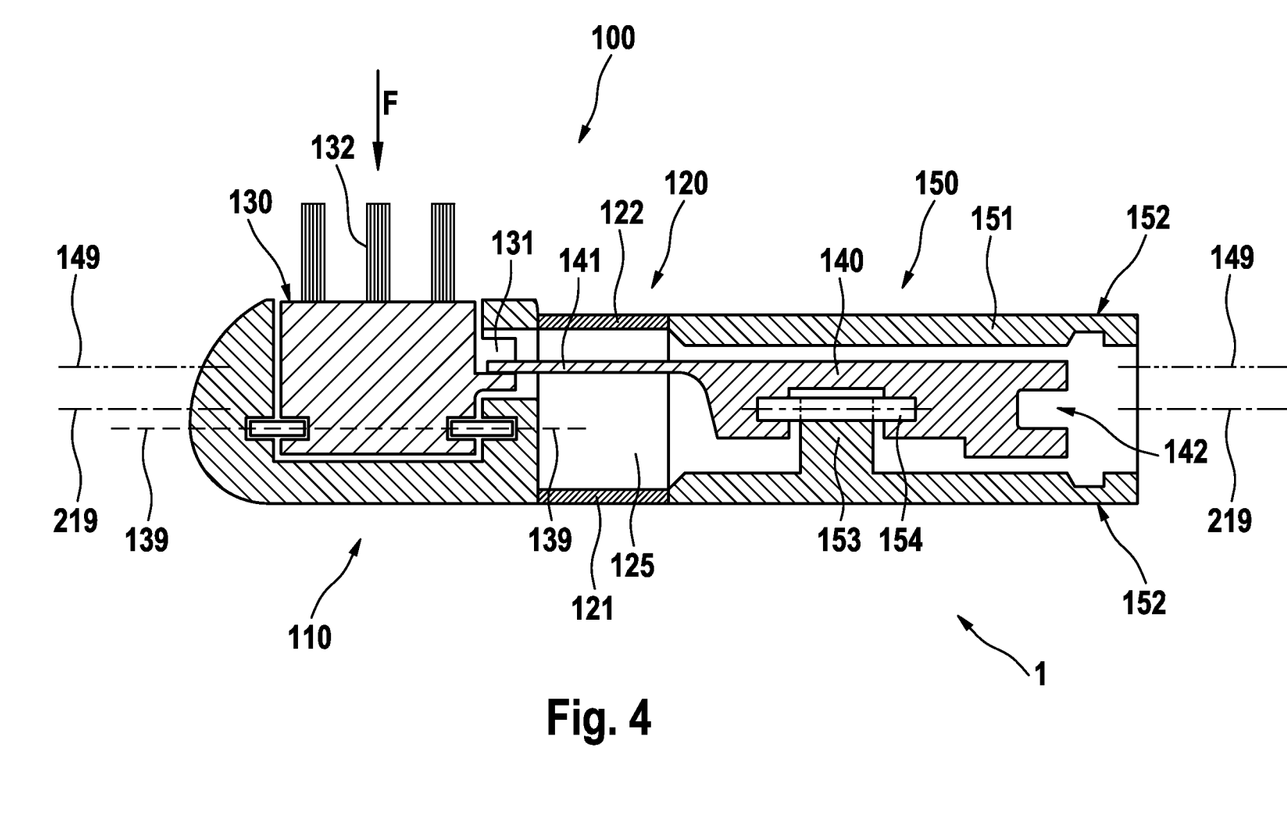
FIG. 4 is a longitudinal cross sectional cut through an example embodiment of an oral care implement having a transmission element according to embodiments shown and described herein.

FIG. 4 shows a longitudinal cross section through an example embodiment of an oral care implement realized as an oral care attachment 100 in accordance with the present disclosure. The oral care attachment 100 includes a head section 110, a neck section 120, and a base section realized as a housing section 150. The head section 110 may comprise a carrier element 130 that is mounted for driven oscillatory movement. At least one cleaning element 132 such as bristle tufts or elastomeric fingers may be mounted at the carrier element 130. The carrier element 130 may be mounted for oscillatory rotation around a carrier axis 139, which carrier axis 139 may be parallel to a longitudinal extension axis of the oral care attachment 100. The neck section is arranged for deformation under a load that is applied at the head section along a use direction F. The base section 150 may comprise a tubular housing 151 that may have a coupling structure 152 at its end distal to the head section 110, which coupling structure 152 is intended for attaching the oral care attachment 100 to a handle section of an oral care device. A transmission element realized by a drive shaft extension element 140 intended for coupling with a drive shaft of a handle section of an oral care device may be mounted at the base section. The drive shaft extension element 140 may be mounted in the tubular hollow of the oral care attachment 100 such that it can rotate around a longitudinal transmission element axis 219. The drive shaft extension element 140 may be mounted on an axle 154 that may be coupled to a projection 153 of the housing 151.

In one embodiment, the axle 154 may extend along the longitudinal transmission element axis 219. The drive shaft extension element 140 may comprise a cam 141 that may be arranged eccentrically with respect to the longitudinal transmission element axis 219. The cam 141 may engage into a slot 131 provided at the carrier element 130 so that the oscillatory movement of the cam 141 around the longitudinal transmission element axis drives the carrier element 130 into an oscillatory movement around the carrier axis 139. The neck section may include a parallel spring arrangement having in particular two parallel arranged spring elements 121 and 122, which spring elements 121 and 122 may in particular extend parallel to the longitudinal transmission element axis 219. The use direction F may be perpendicular to the extension planes of the in particular flat spring elements 121 and 122. For sake of clarity it is noted that the drive shaft extension element 140 forms a transmission element in accordance with the present disclosure. The drive shaft extension element may be intended to couple to a drive shaft of a handle section or directly to a drive unit of a handle section. The coupled drive shaft extension element and the drive shaft together form a transmission element of the oral care device that is formed by attaching the oral care attachment 100 to the handle section. In embodiments, where the drive shaft extension element couples directly to the drive unit, the drive shaft extension element form the transmission element of the oral care device formed by the oral care attachment 100 and the handle section.

In some embodiments, an oral care attachment does not comprise a drive shaft extension element but a carrier element that is intended to engage with a transmission element (for example, drive shaft) of a handle section when the oral care attachment is attached to the handle section to form an oral care device.

Figure 5:
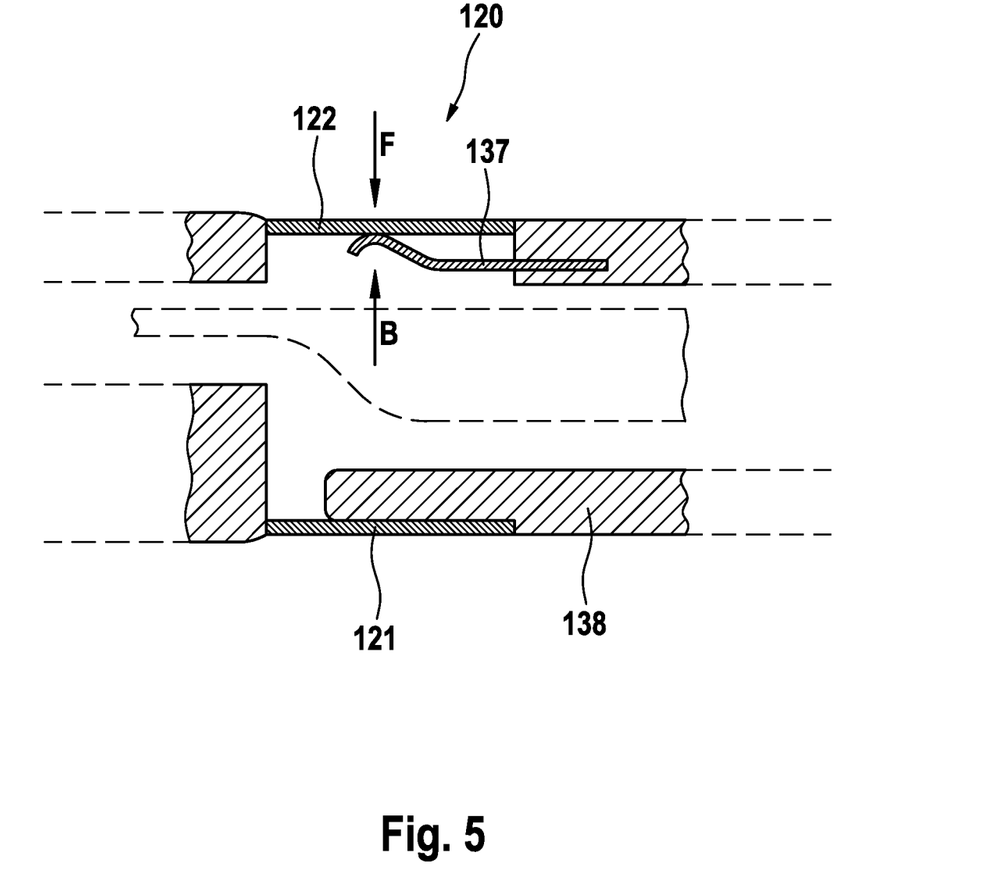
FIG. 5 is a longitudinal cross sectional cut through a neck section comprising a biasing element for defining a first threshold load value that is above 0 Newton according to embodiments shown and described herein.

FIG. 5 is a schematic longitudinal cross section through a neck section 120 of an example embodiment of an oral care implement in accordance with the present disclosure. The section 120 may again include a parallel spring arrangement that in particular has two parallel arranged flat spring elements 121 and 122. In one embodiment, the neck section may include a biasing element 137 that applies a biasing load onto the parallel spring arrangement along a direction B that is opposite to the use direction F. In some embodiments, the parallel spring arrangement may be generally arranged to not deform under the applied biasing load. In some embodiments, a stop element 138 may be utilized to inhibit any or at least a considerable deformation of the neck section 120 under the applied biasing force. In some embodiments, a transmission element (indicated by a dotted line) may be arranged together with a carrier element such that any deformation of the neck section 120 is at least essentially inhibited under the applied biasing load. The biasing element 137 may be realized as a biasing spring, which biasing spring may act against at least one of the spring elements 121 or 122 of the parallel spring arrangement. The biasing spring may be designed such that a deformation of the neck section 120 only occurs in case that the load applied at the head section along the use direction F is larger than a first threshold load value. The first threshold load value may be chosen to lie in a range of between about 0.25 N to about 2.0 N, and in another embodiment, between about 0.5 N and about 1.0 N. Due to the reduction in the oscillation amplitude peak value occurring in some embodiments when the applied load is above the first threshold load value, the user is informed that an appropriate load range is achieved. In an embodiment, where the transmission element decouples from the carrier element when the applied load is above a second threshold load value, the user is then informed that a load is applied that is not anymore appropriate for the oral care treatment action.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care implement comprising:
a head section including a carrier element that is mounted for driven movement around a longitudinal axis of the carrier element;
a base section including a transmission element; and
an at least partly elastically deformable neck section arranged between the head section and the base section;
wherein the transmission element is coupled to the carrier element for driving the carrier element into an oscillatory movement around the longitudinal axis of the carrier element with an oscillation amplitude peak value; and wherein the neck section is arranged as a parallel spring arrangement that deforms when during operation a load above a first threshold load value is applied at the head section along a use direction such that the angular relationship between the head section and the base section is preserved and the head section and the base section move relatively to each other resulting in a reduction of the oscillation amplitude peak value.

2. The oral care implement according to claim 1, wherein the parallel spring arrangement comprises two leaf spring members that are arranged parallel to each other in an unloaded state and that each extend in a direction parallel to a longitudinal extension axis of the oral care implement.

3. The oral care implement according to claim 2, wherein the neck section comprises at least one soft material membrane connecting the two leaf spring members.

4. The oral care implement according to claim 2, wherein at least one of the two leaf spring members is a metal leaf spring.

5. The oral care implement according to claim 1, wherein the first threshold load value is zero Newton.

6. The oral care implement according to claim 1, wherein the first threshold load value is in a range from about 1 Newton to about 2 Newton.

7. The oral care implement according to claim 1, wherein a biasing spring is arranged in the neck section for applying a biasing load in a direction opposite to the use direction.

8. The oral care implement according to claim 7, wherein a stop element essentially inhibits deformation of the neck section under the applied biasing force.

9. The oral care implement according to claim 1, wherein the transmission element decouples from the carrier element when the load applied at the head section along the use direction reaches a second threshold load value.

10. The oral care implement according to claim 9, wherein the second threshold load value is in a range from about 3 Newton to about 5 Newton.

11. The oral care implement according to claim 1, wherein the transmission element moves around and/or moves along a transmission element axis and the carrier element is arranged to be driven around a carrier axis, wherein the minimal transversal distance between the transmission element axis and the carrier axis changes when the neck section is deformed.

12. The oral-care implement of claim 1, wherein the transmission element includes a cam provided on a drive shaft, the cam engaging a slot provided at the carrier element whereby moving the carrier element into an oscillatory motion around the longitudinal axis of the carrier during operation.

13. The oral-care implement of claim 12, wherein the cam has a longitudinal axis substantially parallel to the longitudinal axis of the carrier element and disposed at a distance d1 from the longitudinal axis of the carrier element in an unloaded state, and wherein during operation when the neck section deforms under the applied load the distance d1 between the longitudinal axis of the cam and the longitudinal axis of the carrier element increases to a distance d2, wherein distance d2 is greater than the distance d1.

14. The oral-care implement of claim 13, wherein the increase of the distance between the longitudinal axis of the cam and the longitudinal axis of the carrier element from the distance d1 to the distance d2 causes the oscillation amplitude peak value of the oscillatory movement of the carrier element to decrease relative to that in the unloaded state.

* * * * *